(12) United States Patent
Frayling et al.

(10) Patent No.: US 10,525,459 B2
(45) Date of Patent: Jan. 7, 2020

(54) DROPLET SEQUENCING DEVICE

(71) Applicant: BASE4 INNOVATION LTD, Cambridge, Cambridgeshire (GB)

(72) Inventors: Cameron Alexander Frayling, Cambridge (GB); Thomas Henry Isaac, Cambridge (GB)

(73) Assignee: BASE4 INNOVATION LTD, Cambridge, Cambridgeshire (GB)

( * ) Notice: Subject to any disclaimer, the term of this patent is extended or adjusted under 35 U.S.C. 154(b) by 51 days.

(21) Appl. No.: 15/741,344

(22) PCT Filed: Jul. 6, 2016

(86) PCT No.: PCT/EP2016/065968
§ 371 (c)(1),
(2) Date: Jan. 2, 2018

(87) PCT Pub. No.: WO2017/005789
PCT Pub. Date: Jan. 12, 2017

(65) Prior Publication Data
US 2018/0353949 A1      Dec. 13, 2018

(30) Foreign Application Priority Data
Jul. 6, 2015    (EP) .................................. 15002007

(51) Int. Cl.
*B01L 3/02*       (2006.01)
*C12Q 1/6869*     (2018.01)
(Continued)

(52) U.S. Cl.
CPC ....... *B01L 3/0268* (2013.01); *B01L 3/502715* (2013.01); *C12Q 1/6869* (2013.01);
(Continued)

(58) Field of Classification Search
None
See application file for complete search history.

(56) References Cited

U.S. PATENT DOCUMENTS

| 5,879,944 | A | 3/1999 | Komatsu |
| 6,203,759 | B1 * | 3/2001 | Pelc ....................... B01L 3/0265 222/333 |

(Continued)

FOREIGN PATENT DOCUMENTS

| EP | 2 828 408 | 10/2015 |
| WO | 2014/053853 | 4/2014 |

(Continued)

OTHER PUBLICATIONS

International Search Report dated Sep. 13, 2016 in International Application No. PCT/EP2016/065968.
(Continued)

*Primary Examiner* — Joseph G. Dauner
(74) *Attorney, Agent, or Firm* — Wenderoth, Lind & Ponack, L.L.P.

(57) ABSTRACT

An apparatus for sequencing a nucleic acid by printing droplets at least some of which contain single nucleotides derived from the nucleic acid is provided. It is characterised by comprising; •a planar substrate having a face with droplet-receiving locations arranged in at least one track parallel to a first axis defining the substrate; •a printer head comprising a plurality of droplet-dispensing nozzle groups juxtaposed above the droplet-receiving locations so that each nozzle group can in turn dispense a droplet into the droplet-receiving locations; •a means for stepping the printer head along the first axis relative to the droplet-receiving locations; •a nucleotide-generating site upstream of the printer head by means of which an ordered stream of single nucleotides is created from the nucleic acid and delivered to a first droplet-dispensing nozzle group; •at least one source (Continued)

of incident electromagnetic radiation adapted to illuminate the droplet-receiving locations and •at least one photodetector to detect adapted to detect fluorescence radiation emitted by each droplet-receiving location after illumination.

13 Claims, 3 Drawing Sheets

Specification includes a Sequence Listing.

(51) Int. Cl.
  *B01L 3/00* (2006.01)
  *G01N 35/10* (2006.01)
(52) U.S. Cl.
  CPC ..... *G01N 35/1011* (2013.01); *G01N 35/1074* (2013.01); *B01L 2200/025* (2013.01); *B01L 2200/143* (2013.01); *B01L 2300/0627* (2013.01); *B01L 2300/0819* (2013.01); *C12Q 2563/107* (2013.01); *C12Q 2563/159* (2013.01); *G01N 2035/1041* (2013.01)

(56) References Cited

U.S. PATENT DOCUMENTS

| | | | | |
|---|---|---|---|---|
| 6,569,620 | B1* | 5/2003 | Gold | C12Q 1/6811 422/63 |
| 6,664,044 | B1 | 12/2003 | Sato | |
| 2002/0074342 | A1 | 6/2002 | Shafer | |
| 2004/0021068 | A1 | 2/2004 | Staats | |
| 2004/0203173 | A1 | 10/2004 | Peck et al. | |
| 2007/0015289 | A1 | 1/2007 | Kao et al. | |
| 2011/0127292 | A1* | 6/2011 | Sarofim | B01L 9/52 422/521 |
| 2016/0040224 | A1 | 2/2016 | Frayling et al. | |
| 2016/0122802 | A1 | 5/2016 | Frayling | |

FOREIGN PATENT DOCUMENTS

| | | | |
|---|---|---|---|
| WO | 2014/053854 | 4/2014 | |
| WO | 2014/167323 | 10/2014 | |
| WO | 2014/199113 | 12/2014 | |
| WO | 2015/121675 | 8/2015 | |
| WO | 2015/185564 | 12/2015 | |
| WO | 2016/012789 | 1/2016 | |
| WO | WO-2016116757 A1 * | 7/2016 | ............ B01L 3/0268 |

OTHER PUBLICATIONS

Written Opinion of the International Searching Authority dated Sep. 13, 2016 in International Application No. PCT/EP2016/065968.

* cited by examiner

```
                        SEQUENCE LISTING

<160> NUMBER OF SEQ ID NOS: 2

<210> SEQ ID NO 1
<211> LENGTH: 40
<212> TYPE: DNA
<213> ORGANISM: Artificial sequence
<220> FEATURE:
<223> OTHER INFORMATION: oligonucleotide 1
<220> FEATURE:
<221> NAME/KEY: misc_feature
<222> LOCATION: (26)..(26)
<223> OTHER INFORMATION: deoxythymidine nucleotide (T) labelled with
      Atto 655 dye
<220> FEATURE:
<221> NAME/KEY: misc_feature
<222> LOCATION: (27)..(27)
<223> OTHER INFORMATION: deoxythymidine nucleotide (T) labelled with
      Atto 655 dye
<220> FEATURE:
<221> NAME/KEY: misc_feature
<222> LOCATION: (28)..(28)
<223> OTHER INFORMATION: deoxythymidine nucleotide labelled with a BHQ-2
      quencher
<220> FEATURE:
<221> NAME/KEY: misc_feature
<222> LOCATION: (29)..(29)
<223> OTHER INFORMATION: deoxythymidine nucleotide (T) labelled with
      Atto 655 dye
<220> FEATURE:
<221> NAME/KEY: misc_feature
<222> LOCATION: (30)..(30)
<223> OTHER INFORMATION: deoxythymidine nucleotide (T) labelled with
      Atto 655 dye

<400> SEQUENCE: 1
tcgtgcctca tcgaacatga cgaggttttt ggtttgtggt                          40

<210> SEQ ID NO 2
<211> LENGTH: 115
<212> TYPE: DNA
<213> ORGANISM: Artificial sequence
<220> FEATURE:
<223> OTHER INFORMATION: oligonucleotide 2
<220> FEATURE:
<221> NAME/KEY: misc_feature
<222> LOCATION: (1)..(1)
<223> OTHER INFORMATION: 5' phosphate group attached to cytosine

<400> SEQUENCE: 2
catgttcgat gaggcacgat agatgtacgc tttgacatac gctttgacaa tacttgagca    60
gtcggcagat ataggatgtt gcaagctccg tgagtcccac aaaccaaaaa cctcg        115
```

DROPLET SEQUENCING DEVICE

This invention relates to an improved droplet sequencing device and method in which single nucleotides are printed onto a substrate before being captured by an oligonucleotide probe system and identified using fluorescence spectroscopy.

In our previously filed patent applications WO2014053854 and WO2014167323 we have disclosed a method for sequencing nucleic acids such as synthetic and naturally occurring DNA and RNA by a method which involves first creating an ordered stream of single nucleotides from the corresponding precursor analyte for example by progressive pyrophosphorolysis or exonucleolysis. Thereafter, the single nucleotides are captured in aqueous microdroplets where they are treated with a quenched, fluorophore-labelled oligonucleotide probe system which, after capture occurs, undergoes progressive exonucleolysis to liberate single nucleotides bearing free fluorophores whose characteristic fluorescence emissions enable the nucleotide originally captured to be reliably identified. Examples of probes and methods suitable for this purpose have been described in WO2014053853, WO2015121675, WO2015185564, WO2016012789 and the above-mentioned patents.

Whilst the method described above can be carried out by creating and manipulating a stream of the droplets dispersed for example in an immiscible carrier medium such as silicone oil, we have recently found that the method can advantageously and more effectively performed by printing the droplets directly onto the surface of a substrate as they are formed. This method is the subject of our recently filed application WO2014199113. In pursuance of this, we have now developed a design for the apparatus itself which is especially advantageous for analysing nucleic acid fragments having a significant nucleotide length (for example in excess of 100 nucleotides).

US2007015289 discloses a method for dispensing multiple droplets but is not directed to the sequencing of nucleic acids using microdroplets and makes no mention of the creation of single nucleotides. Furthermore, the length scales and volumes would be unsuitable for use in our particular application. Further spotting devices and dispensing and interface arrays are described in U.S. Pat. No. 5,879,944, US2002074342 and US2004021068 but these are also not directed towards sequencing.

Thus, according to the present invention, there is provided an apparatus for sequencing a nucleic acid by printing droplets at least some of which contain single nucleotides derived from the nucleic acid characterised by comprising;
- a planar substrate having a face with droplet-receiving locations arranged in at least one track parallel to a first axis defining the substrate;
- a printer head comprising a plurality of droplet-dispensing nozzle groups juxtaposed above the droplet-receiving locations so that each nozzle group can in turn dispense a droplet into the droplet-receiving locations;
- a means for stepping the printer head along the first axis relative to the droplet-receiving locations;
- a nucleotide-generating site upstream of the printer head by means of which an ordered stream of single nucleotides is created from the nucleic acid and delivered to a first droplet-dispensing nozzle group;
- at least one source of incident electromagnetic radiation adapted to illuminate the droplet-receiving locations and
- at least one photodetector adapted to detect fluorescence radiation emitted by each droplet-receiving location after illumination.

The planar substrate employed in the apparatus of the invention is suitably a sheet of resilient material which has a face with a plurality, suitably many tens, hundreds, thousands or millions, of droplet-receiving locations capable of holding droplets printed thereon in place. In one embodiment, these locations are virtual locations and are created as the printer head prints droplets. In another, they are patterned onto the face and for example comprise depressions in the face of the substrate (e.g. wells) or cups formed thereon. In another embodiment, the droplet-receiving locations are coated with a hydrophilic material to further enhance the adherence of the droplet to the substrate. In yet another embodiment the depressions or cups are hemispherical in morphology with a maximum cross-section in the micrometre range. Preferably the substrate is at least optically transparent at each droplet-receiving location although it is also contemplated that the whole substrate may comprise an optically transparent sheet such as quartz, glass or clear plastic.

The droplet-receiving locations may if so desired be provided with one or more holes in the bottom to enable the contents thereof to be drained away after having been interrogated. If this embodiment is used, it is preferred to initially stop up each hole with a plug of high melting material; for example a wax which can be melted away when the time comes.

In one embodiment, the droplet-receiving locations are arranged in the form of a linear track running parallel to a first axis of the face of the substrate along which the printer head is stepped. In a preferred embodiment, the substrate is provided with a plurality of such tracks running parallel to each other thereby creating a rectangular array. In another, the plurality of tracks may be grouped together to form higher order track-structures each of which corresponds to one traverse of the printer head across the face.

In addition to the track(s) of droplet-receiving locations the substrate may possess one or more lips running around its extremities or areas therein to ensure that a preferred droplet-immiscible solvent coating it is held in place. In another embodiment, either side of the tracks runs a means to ensure that the printer head remains precisely located over the droplet-receiving locations as it moves over the substrate. In one arrangement, this means comprises a pair of profiled rails running parallel to the tracks which can cooperate with corresponding profiles on wheels, grooves or the like on the printer head. This, however, is only one example of many possible arrangements which will easily occur to the skilled man; for example the mirror-image arrangement where the rails are located on the printer heads and the wheels or grooves on the substrate will be immediately apparent and are included within the scope of the invention.

Turning to the printer head this comprises a plurality of droplet-printing nozzle groups which, when the printer head is in use, are juxtaposed immediately above the droplet-receiving locations so that each nozzle can in turn cause a droplet to be dispensed thereinto. Each nozzle group may consist of a single nozzle or a plurality of like nozzles. Dispensing can be caused to occur by any of the known means in the art including for example by electrical or electrostatic means. Since the dimensions of the droplets preferably have dimensions in the micrometre range it is preferred that the nozzles are similarly dimensioned. In one embodiment, the nozzles in a given group are connected to a reservoir or a microfluidic system for dispensing materials.

In one preferred embodiment, each nozzle group comprises a plurality of nozzles and each nozzle in a given nozzle group is arranged in line along a second axis perpendicular to the first axis of the face of the substrate and wherein the distance between each adjacent nozzle in said line is the same or an integral multiple of the distance between adjacent droplet-receiving locations in adjacent tracks. In this embodiment, lines of nozzles representing a given nozzle group are arranged in parallel one behind the other to enable each droplet location in a track to be filled sequentially with liquid issuing from nozzles in each droplet group.

In another preferred embodiment the printer head comprises at least first and second nozzle groups wherein the first group dispenses aqueous droplets at least some of which contain a single nucleotide; suitably a nucleotide monophosphate, a nucleotide diphosphate or most preferably a nucleotide triphosphate and the second nozzle group dispenses one or more, preferably four different oligonucleotide probe systems having the characteristics described in one of WO2014053853, WO2014167323, WO2015121675, WO2015185564 and WO2016012789 the contents of which are herein incorporated by reference and further discussed below.

Briefly, these probe system comprise one or more oligonucleotide components at least one of which includes one or more fluorophores which in the probe systems' unused state are essentially quenched and non-fluorescing. Once the probes have captured the single nucleotide they are selective for, they become susceptible to progressive exonucleolytic degradation thereby releasing fluorophore-labelled nucleotides which are unquenched.

Typically the second nozzle group will dispense aqueous droplets comprising the probe systems and the various reagents required to cause the capture reaction and optionally the degradation to occur including a polymerase, a ligase and optionally the exonuclease. However it is contemplated that these components may be introduced separately into the droplet-receiving locations by means of one or more further nozzle groups if so desired. Thus, in a preferred embodiment, the first and second nozzle groups may be augmented by one or more third nozzle groups which dispense droplets containing an enzyme. For example where the droplets dispensed by the first nozzle group contain single nucleotide triphosphates generated by progressive pyrophosphorolysis of a precursor DNA or RNA analyte the third nozzle group can be used to introduce droplets containing a pyrophosphatase into the droplet-receiving location in order to destroy any pyrophosphate present along with the nucleotide triphosphate before the probe system is introduced. In this particular instance, the third nozzle group is conveniently located between the first and second nozzle group on the printer head. However this embodiment is not to be construed as limiting and it may well be desirable to introduce other enzymes at other points in the printing process; e.g. the exonuclease referred to above.

The nozzles associated with each nozzle group may be provided with heater or cooler elements to heat or cool any liquid before it issues forth from the nozzle. This is particularly useful to ensure that at any given point in the printing the contents of the droplet-receiving locations are at the optimum temperature.

The printer head may also further comprise a dispenser for dispensing a water-immiscible coating onto the face of the substrate bearing the droplet-receiving locations prior to use. In one embodiment this liquid comprises oil, e.g. silicone oil, optionally containing one or more surfactants. In another embodiment this oil is a liquid at a relatively high temperature but can be frozen into a solid wax when printing is complete. This has the advantage of further confining the contents of the droplet receiving location in a solid matrix whilst for example analysis of the contents is taking place.

The printer head may also contain at least one second dispenser for dispensing cleaning fluid onto the face of the substrate bearing the droplet-receiving locations. This enables the substrate to be cleaned between runs making it reusable.

Suitably the means for stepping the printer head comprises a microprocessor-controlled motor for driving wheels located on the underside of the printer head and which engage with the tracks or more preferably a linear translation stage or stepper motor which moves it relative to the substrate (or vice versa).

In accordance with the sequencing method used with the apparatus of the present invention, the apparatus comprises a nucleotide-generating site upstream of the printer head by means of which an ordered stream of single nucleotides is created from the nucleic acid and delivered to a first droplet-dispensing nozzle group in the printer head. This ordering of this stream corresponds to the sequence of nucleotides in the nucleic acid. In one embodiment this site is located in a chamber provided with an analyte-receiving location where the nucleic acid can be held, for example a cup adapted to receive and hold in place a bead to which the nucleic acid is attached; e.g. by suction. The chamber is further provided with fluidic inlets and outlets; the latter being connected to the printer head and by means of which a flowing aqueous medium can be introduced and removed; for example by microfluidic tubing. In another embodiment the nucleic acid is caused to undergo progressive pyrophosphorolysis at the site to form an ordered stream of nucleotide triphosphates in the presence of an enzyme and a flowing aqueous stream further comprising pyrophosphate and those other reagents required to effect this reaction in accordance with the teachings of those of our patents referred to above.

The source used to illuminate the droplet-receiving locations with electromagnetic radiation is suitably a plasma lamp, a halogen lamp or preferably a laser or an LED operating at a frequency which will stimulate the free fluorophores generated at the droplet-receiving location. In one embodiment, the printer head and this source are located on the same side of the substrate but in a more preferred embodiment they are located on opposite sides so that the incident radiation is transmitted through the optically-transparent substrate. Likewise the photodetector can be located on the same or opposite sides of the substrate as the source but preferably it is located on the opposite side. In such a case the photodetector may be made integral with the printer head so that it moves therewith as the face is traversed. The photodetector used can be any type which is able to detect radiation frequency(s) characteristic of the different fluorophores used.

In addition to the above-mentioned components, the apparatus may include other items such as ancillary optics (e.g. mirrors, waveguides, filters and lenses to manipulate and focus beams of the incident and fluorescence radiation), microfluidic piping, and one or more microprocessors for controlling some or all of the following functions; addition and timing of the droplets into the droplet-receiving locations, timing of the illumination and interrogation of the droplet-receiving locations and analysis of any signal produced by the photodetector. Such analysis may however be conducted on a stand-alone computer if so desired.

In a second aspect of the invention there is provided a method suitable for use with the apparatus. It comprises a method of sequencing a nucleic acid characterised by comprising the steps of (1) delivering an aqueous medium containing an ordered stream of single nucleotides derived from the nucleic acid to a first droplet nozzle group of a printer head; (2) printing a first droplet, containing a single nucleotide, from the first droplet nozzle group into at least one droplet-receiving location on a planar substrate; (3) thereafter printing into the same droplet-receiving locations a second aqueous droplet containing at least one probe system comprising an oligonucleotide labelled with fluorophores wherein the fluorophores are only detectable after release by exonucleolysis; a polymerase and a ligase; (4) allowing the fluorophores to be released at the droplet-receiving location(s); (5) illuminating the droplet-receiving location(s) with incident electromagnetic radiation and detecting fluorescence radiation characteristic of the single nucleotide emitted therefrom.

In one embodiment of this method the nucleic acid is a synthetic or naturally-occurring DNA or RNA or fragment thereof; in another the single nucleotides are nucleotide triphosphates which have been generated by progressive pyrophosphorolysis of the nucleic acid. In the case of this latter embodiment, the method preferably further comprises between steps (2) and step (3) the additional step of printing a third aqueous stream containing a pyrophosphatase into the droplet-receiving location to consume residual pyrophosphate. In yet another embodiment of the method generally either the second droplet further contains an exonuclease or alternatively a fourth aqueous droplet containing an exonuclease is printed into the droplet-receiving location between steps (3) and (4).

In all the embodiments of the method described above the probe systems employed may be selected from any of those described in in WO2014053853, WO2014167323, WO2015121675, WO2015185564 and WO2016012789 the contents of which should be referred to by the skilled man and are herein incorporated by reference. However in a first preferred aspect, the probe system comprises one of a class of pairs of first and second oligonucleotides. The first oligonucleotide in such a pair preferably comprises (a) a first double-stranded region and (b) a second single-stranded region comprised of n nucleotide bases wherein n is greater than 1 preferably greater than 5. In one sub-class, the first oligonucleotide can be regarded as having a molecular structure derived from a notional or actual single-stranded oligonucleotide precursor where the double-stranded region has been created by partially folding the 3' end of the precursor back on itself to generate a configuration which can be termed 'j shaped'. In another sub-class, the first oligonucleotide is generated by hybridising a third, shorter single-stranded oligonucleotide onto the 3' end of a longer fourth single-stranded oligonucleotide and then rendering the end of the resulting molecule which is double-stranded 'blunt' by means of a protecting group which for example bridges the final nucleotides of the two strands. Typically, the total length of the first oligonucleotide is up to 150 nucleotide bases, preferably between 20 and 100 nucleotide bases. At the same time it is preferred that the integer n is between 5 and 40, preferably between 10 and 30.

As regards the second oligonucleotide in the pair, this is single-stranded and suitably has a nucleotide base sequence which is wholly or partially the compliment of that of the single-stranded region of the first oligonucleotide starting one nucleotide base beyond the end of the double-stranded region. The length of the second oligonucleotide is not critical and can be longer or shorter than the single-stranded region to which it can bind although it is preferably not n−1 nucleotide bases long. More preferably, the length of the second oligonucleotide is chosen so that in the captured molecule a short overhang of unpaired nucleotide bases (e.g. 2 to 10 nucleotide bases) remains on one or other of the two strands thereof. Preferably, in this class the fluorophores are located on the second oligonucleotide. Probe systems of this class work by attaching the single nucleotide base to the double-stranded end of the first oligonucleotide and hybridising the second oligonucleotide onto the remaining single-stranded region to generate a captured molecule which is double-stranded apart from its overhang.

In a second preferred aspect, the probe system comprises a class of single oligonucleotides each consisting of a single-stranded nucleotide region the ends of which are attached to two different double-stranded regions. Here, the single-stranded nucleotide region is comprised of one nucleotide base only making the probe extremely selective for the detection of the target i.e. the complimentary single nucleotide base in the droplet.

Turning to the double-stranded oligonucleotide region(s), it is preferred that they are derived or derivable from two oligonucleotide precursors, each preferably closed looped, or from a common single-stranded oligonucleotide precursor by folding the latter's ends back on themselves to create two closed-loop oligonucleotide base regions with an intermediate gap constituting the single-stranded nucleotide region. In all cases the effect is the same; adjacent to the ends of the single-stranded nucleotide region will be 3' and 5' free ends on the other strand of the oligonucleotide region to which the corresponding 5' and 3' ends of the target can be attached. Thus use of the probe system involves a process of attaching the single-stranded nucleotide region to the target single nucleotide base by joining up the available 3' and 5' ends of the probe system to generate a used probe system which is double-stranded along its whole length.

Suitably, the double-stranded oligonucleotide region(s) are up to 50 nucleotide base pairs long, preferably up to 45 nucleotide base pairs, more preferably in the range 5 to 40 nucleotide base pairs and most preferably in the range 10 to 30. Longer regions may be used but the potential risk that access to the single-stranded nucleotide region by the target may become restricted through entanglement. This makes this embodiment potentially less attractive.

In this embodiment it is preferred that the fluorophores bound to the double-stranded oligonucleotide region(s) are located remote from the single-stranded nucleotide region. Finally in one embodiment it is preferred that at least one of the double-stranded oligonucleotide regions comprises at least one restriction enzyme recognition site preferably adjacent the region where the fluorophores are located or clustered. For these probe systems, liberation of the fluorophores comes about by first a restriction enzyme exhibiting endonucleolytic behaviour and making a double-stranded cut in the used probe system at the site mentioned above. The short fragments so created may then be degraded further by the exonuclease into single nucleotides at least some of which will be labelled with fluorophores. Thus, when the used probe system comprises multiple fluorophores this leads to the release of a cascade of fluorophores which, by virtue of them now being separated from each other and/or their associated quenchers, are now free to fluoresce in the normal way. Such a restriction enzyme recognition site will typically comprise a specific sequence of from 2 to 8 nucleotide pairs. In another preferred embodiment the restriction enzyme recognition site will be one created by binding of the single nucleotide to the single-stranded nucleotide region.

In a third preferred aspect the probe system is comprised of three components; (a) a first single-stranded oligonucleotide labelled with fluorophores in an undetectable state and (b) second and third unlabelled single-stranded oligonucleotides capable of hybridising to complementary regions on the first oligonucleotide. In one embodiment the second and third oligonucleotides are discrete entities whilst in another they are linked to each other by means of a linker region. In this latter case, in one embodiment the linker region links ends of the second and third oligonucleotides; preferably the 5' end of the second and the 3' end of the third oligonucleotide. The linker region can in principle be any divalent group but is conveniently another single- or double-stranded oligonucleotide fragment. In one embodiment the linker region is unable to hybridise substantially to the first oligonucleotide.

The first, second and third oligonucleotides are chosen so that the second and third oligonucleotides can hybridise respectively to 3' side and 5' side flanking regions on the first oligonucleotide which themselves are juxtaposed either side of a capture region which comprises the single nucleotide whose nucleotide base is complementary to the one borne by the nucleotide triphosphate to be detected. This makes the three-component probe system highly selective for that particular nucleotide triphosphate. Thus, for example, if the analyte is derived from DNA and the first, second and third oligonucleotides are deoxyribonucleotides, the capture region will be highly selective for deoxyadenosine triphosphate if the nucleotide it comprises bears a thymine base.

Typically, the first oligonucleotide is up to 150 nucleotides long, preferably between 20 and 100 nucleotides. In one embodiment the second oligonucleotide is longer than the complementary 3' side flanking region of the first oligonucleotide by up to 10 preferably from 1 to 5 nucleotides. In another, there is a single nucleotide mismatch between the 3' end of the first oligonucleotide and the nucleotide opposite it on the second oligonucleotide to prevent the nucleotide triphosphate being captured by the polymerase at this point. In yet another embodiment the 3' end of the third oligonucleotide includes an element resistant to exonucleolytic degradation to ensure that the fourth oligonucleotide produced in step (3) is not itself subsequently digested. This can be achieved for example by way of incorporating one or more phosphorothioate linkages, a G-Quadruplex, a boronated nucleotide, an inverted dT or ddT, a C3 spacer or a phosphate group at or near that particular end.

Use of the this third class of probe system generates a double-stranded used probe whose constituent strands are respectively the first oligonucleotide and a complementary fourth oligonucleotide which when read in its 5'-3' direction is comprised of the second oligonucleotide, then a nucleotide derived from the single nucleotide triphosphate and finally the third oligonucleotide. If the second and third oligonucleotides have previously been joined together by a linker region then it will be readily apparent that the fourth oligonucleotide will comprise a closed loop strand that is highly resistant to exonucleolysis. This closed loop can then be used to bind to a further first oligonucleotide enabling further fluorophores to be liberated; thereby creating a cyclic process which grows the fluorescence signal intensity.

In all three aspects of the probe system at least one of the oligonucleotide components in the probe system is multiply labelled with its own unique type of fluorophores and these fluorophores are substantially undetectable when the probe system is in an unused state. Thus, although a fluorophore may exhibit general, low-level background fluorescence across a wide part of the electromagnetic spectrum, there will typically be one or a small number of specific wavelengths or wavelength envelopes where the intensity of the fluorescence is at a maximum. It is at one or more of these maxima where the fluorophore is characteristically detected that essentially no fluorescence should occur. In the context of this patent, by the term 'essentially non-fluorescing' or equivalent wording is meant that the intensity of fluorescence of the total number of fluorophores attached to the probe system at the relevant characteristic wavelength or wavelength envelope is less than 25%; preferably less than 10%; more preferably less than 1% and most preferably less than 0.1% of the corresponding intensity of fluorescence of an equivalent number of free fluorophores.

In principle, any method can be used to ensure that in the probe systems' unused state the fluorophores are essentially non-fluorescing. One approach is to additionally attach quenchers in close proximity to them. Another is based on the observation that when multiple fluorophores are attached in close proximity to each other they tend to quench each other sufficiently well that the criterion described in the previous paragraph can be achieved without the need for quenchers. In this context of this patent, what constitutes 'close proximity' between fluorophores or between fluorophores and quenchers will depend on the particular fluorophores and quenchers used and possibly the structural characteristics of the oligonucleotide to which it is bound. Consequently, it is intended that this term should be construed with reference to the required outcome rather than any particular structural arrangement of the various elements. However, and for the purposes of providing exemplification only, it is pointed out that when adjacent fluorophores or adjacent fluorophores and quenchers are separated by a distance corresponding to the characteristic Förster distance (typically less than 5 nm) sufficient quenching will generally be achieved.

Suitably the relevant component of the probe systems mentioned above is labelled with at least 1, preferably up to 20 fluorophores. To obtain maximum advantage, it is preferred that this component is labelled with at least 2 preferably at least 3 fluorophores. Consequently, ranges constructed from any permutation of these maxima and minima are specifically envisaged herein. If quenchers are employed, it is likewise preferred that this component is labelled with up to 20, preferably up to 10 and most preferably up to 5 of the same.

As regards the fluorophores themselves, they can in principle be chosen from any of those conventionally used in the art including but not limited to xanthene moieties e.g. fluorescein, rhodamine and their derivatives such as fluorescein isothiocyanate, rhodamine B and the like; coumarin moieties (e.g. hydroxy-, methyl- and aminocoumarin) and cyanine moieties such as Cy2, Cy3, Cy5 and Cy7. Specific examples include fluorophores derived from the following commonly used dyes: Alexa dyes, cyanine dyes, Atto Tec dyes, and rhodamine dyes. Examples also include: Atto 633 (ATTO-TEC GmbH), Texas Red, Atto 740 (ATTO-TEC GmbH), Rose Bengal, Alexa Fluor™ 750 $C_5$-maleimide (Invitrogen), Alexa Fluor™ 532 $C_2$-maleimide (Invitrogen) and Rhodamine Red $C_2$-maleimide and Rhodamine Green as well as phosphoramadite dyes such as Quasar 570. Alternatively, a quantum dot or a near infra-red dye such as those supplied by LI-COR Biosciences can be employed. The fluorophore is typically attached to the relevant oligonucleotide component via a nucleotide base using chemical methods known in the art.

Suitable quenchers include those which work by a Förster resonance energy transfer (FRET) mechanism. Examples of commercially available quenchers which can be used in association with the above mentioned-fluorophores include but are not limited to DDQ-1, Dabcyl, Eclipse, Iowa Black FQ and RQ, IR Dye-QC1, BHQ-0, BHQ-1, -2 and -3 and QSY-7 and -21.

As mentioned above the capture of the single nucleotide triphosphate by the probe systems described above is suitably carried out at the droplet-receiving location in the presence of a ligase and a polymerase in at a temperature in the range 20 to 80° C. with the exonucleolysis reaction occurring in the range 30 to 100° C.

The apparatus of the present invention, which is especially suitable for sequencing long-chain DNA or RNA derived from naturally-occurring sources, is now illustrated by the following example in which.

Figure 1:
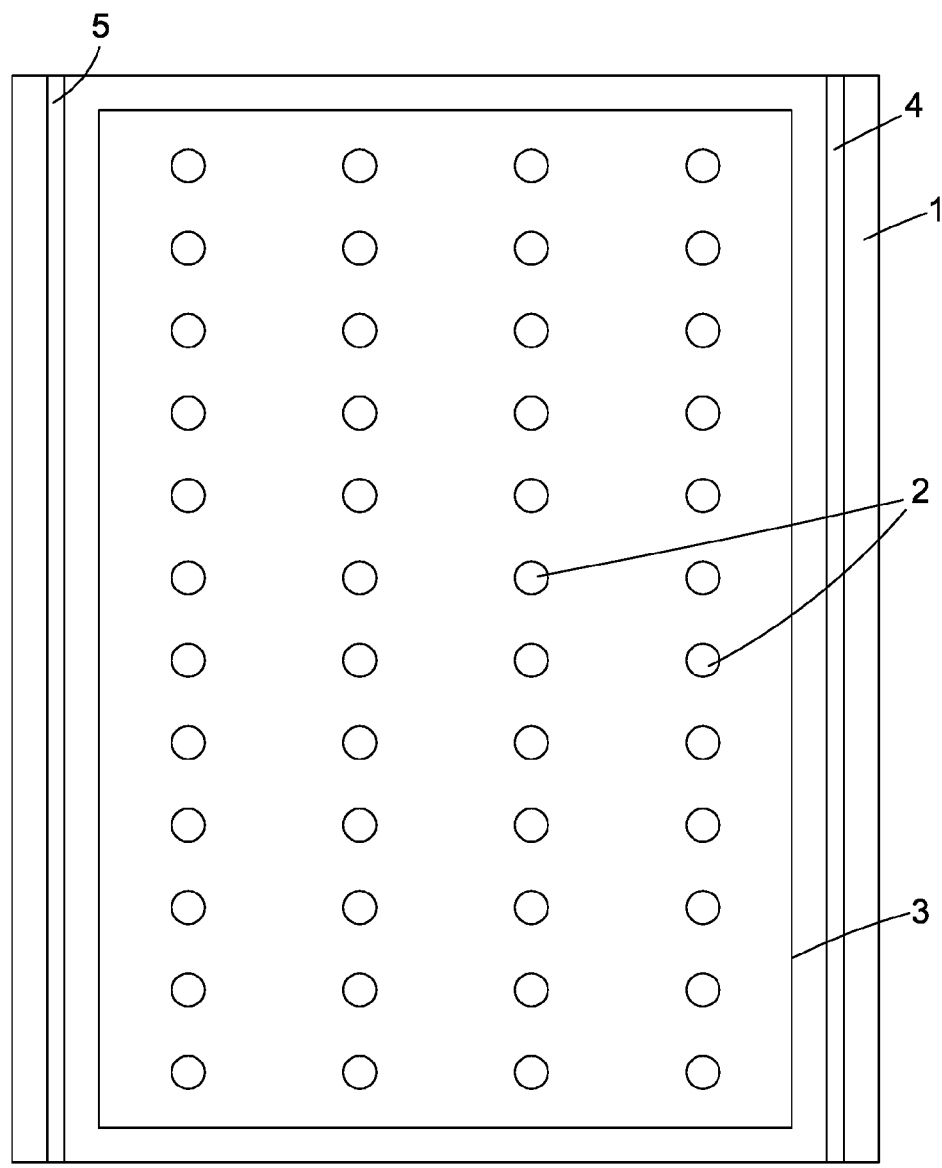
FIG. 1 shows a plan view of a substrate used in the apparatus.
Figure 2A:
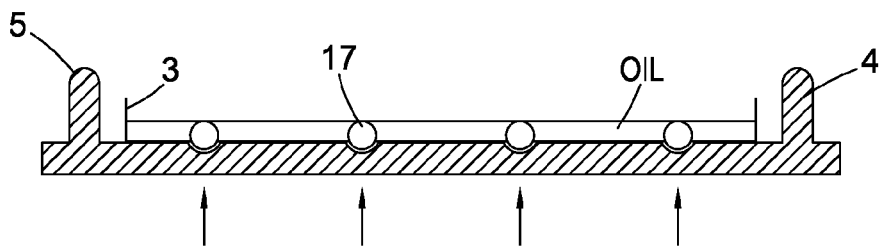
FIGS. 2a and 2b show transverse sections of the substrate along the line X-X.
Figure 2B:
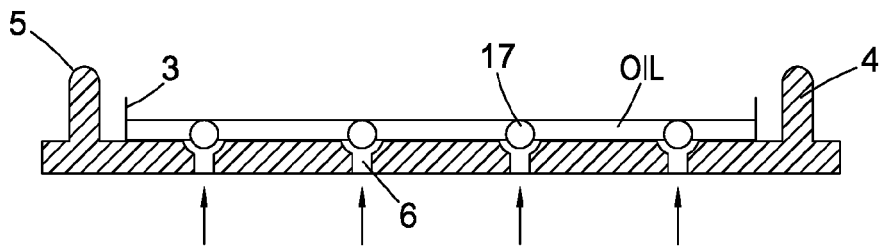

With reference to FIG. 1 a planar substrate according to the present invention comprises a sheet of transparent quartz 1 patterned with an 11×4 rectangular array of hemispherical wells 2 which function as droplet-receiving locations. The whole array is surrounded by a lip 3 to contain oil and rails 4 and 5 profiled to receive the wheels of the printer head. FIGS. 2a and 2b show two different cross-sections of a typical substrate. In FIG. 2a the wells do not extend completely through 1 whilst in FIG. 2b 1 is provided with perforations stopped up by wax 6 which is solid at room temperature but which melts away when the sheet is heated to in excess of 80° C. Each of 2 also includes a micro-heating element (not shown) to enable the temperature of the contents to be controlled. In use, the underside of 1 is illuminated in the direction shown by light from an LED (also not shown).

Figure 3:
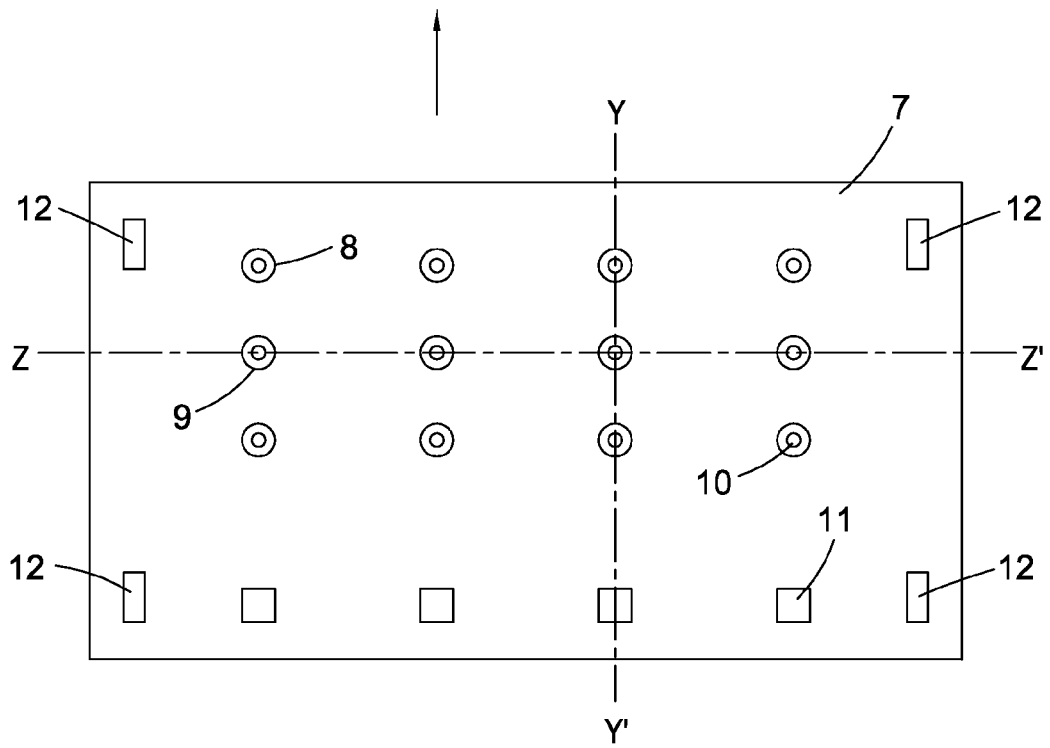
FIG. 3 shows an underside view of the printer head.

FIG. 3 shows a plan view of the underside of the printer head 7, it comprises a 3×4 array of nozzles corresponding to first, third and second nozzle groups 8, 9, 10 arranged in transverse rows which, when 7 is in use, correspond to corresponding transverse rows of 2 on 1. In this particular embodiment, a line of photodetectors 11 are made integral with 7 and likewise arranged in a corresponding transverse row on 7 spaced apart from the nozzles. The underside of 7 finally includes four grooved wheels 12 designed to be locatable on 4 and 5 and driven by an electric motor (not shown) in order to enable 7 to be stepped across 1 in the direction shown by the arrow.

Figure 4:
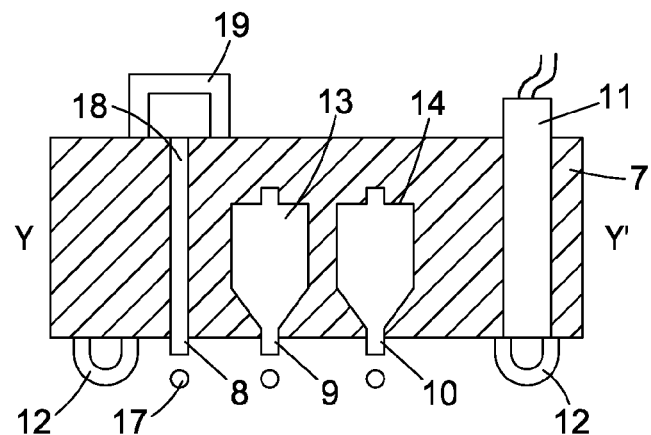
FIG. 4 shows a longitudinal section of the printer head in use along the line Y-Y and FIG. 5 shows a transverse section of the printer head along the line Z-Z.
Figure 5:
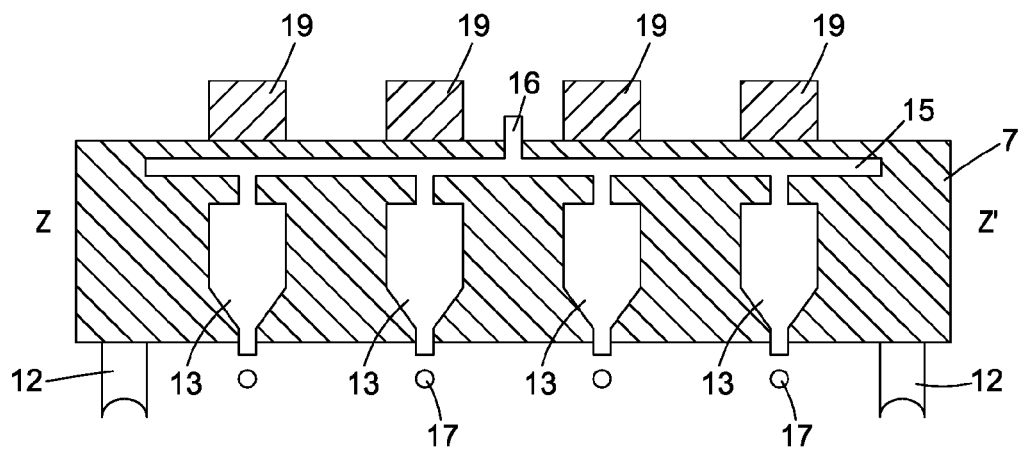

FIGS. 4 and 5 show sectional profiles of 7 along the planes defined respectively by the lines Y-Y' and Z-Z'. From these illustrations, it can be seen that each of the nozzle groups 9 and 10 in the array are connected to corresponding reservoirs 13, 14 and that each reservoir of a given group is connected to others of the same group by microfluidic piping 15 and an inlet 16. 16 may be connected to a pressure-driven pump or piezo-actuator or made subject to an electric field which can be operated to cause droplets 17 to emerge from the various nozzles. Each first nozzle group is separately connected by its own microfluidic pipe 18 to a nucleotide generating site 19 in which a stream of nucleotide triphosphates in aqueous medium are generated from a DNA sample by progressive pyrophosphorolysis by a polymerase. The aqueous medium is then introduced into 18 by positive pressure, thereby causing droplets to emerge from 8 for printing into 2. The droplets are caused to emerge from 8 at a rate such that very few droplets contain more than one nucleotide triphosphate. In practice this may mean that droplets may emerge which contain no nucleotide triphosphates. Generally, the droplets are caused to emerge from 8, 9 and 10 at a rate which are synchronised by a microprocessor (not shown) with the movement of 7 across the array of 2 on 1. In the embodiment shown nozzle group 9 dispenses aqueous droplet containing thermostable inorganic pyrophosphatase (TPP) whilst nozzle group 10 dispenses aqueous droplets containing a probe system of the group described below in the Example. In use, once each 2 is filled by droplets from 8, 9 and 10 and incubation has occurred, fluorescence characteristic of the nucleotide triphosphate it originally contained is measured by each of 11 as it traverses 1. This in turn generates an electrical signal which is fed to a microprocessor or stand-alone computer (not shown) for analysis.

Example of a Probe System for Use in the Apparatus (Ex GB1412977.9)

A first, single-stranded oligonucleotide was prepared, having the following nucleotide sequence:

(SEQ ID NO: 1)
5'TCGTGCCTCATCGAACATGACGAGGXXQXXGGTTTGTGGT3' wherein A, C, G, and T represent nucleotides bearing the relevant characteristic nucleotide base of DNA; X represents a deoxythymidine nucleotide (T) labelled with Atto 655 dye using conventional amine attachment chemistry and Q represents a deoxythymidine nucleotide labelled with a BHQ-2 quencher. It further comprises a capture region (A nucleotide) selective for capturing deoxythymidine triphosphate nucleotides (dTTPs) in a mixture of deoxynucleotide triphosphates (dNTPs). Thereafter three other versions of the first oligonucleotide were prepared wherein each (T) nucleotide was labelled with another different dye and the capture region was respectively a T, G and C nucleotide selective for respectively deoxyadenosine triphosphate (dATP), deoxycytidine triphosphate (dCTP) and deoxyguanosine triphosphate (dGTP).

A second, single-stranded oligonucleotide comprising (1) a second oligonucleotide region having a sequence complementary to the 3' end of the first oligonucleotide with a single base mismatch; (2) a third oligonucleotide region having a sequence complementary to the 5' end of the first oligonucleotide and (3) a 76 base pair single-stranded linker region, was also prepared. It had the following nucleotide sequence:

(SEQ ID NO: 2)
5'PCATGTTCGATGAGGCACGATAGATGTACGCTTTGACATACGCTTTGA
CAATACTTGAGCAGTCGGCAGATATAGGATGTTGCAAGCTCCGTGAGTCC
CACAAACCAAAAACCTCG3' wherein additionally P represents a 5' phosphate group.

A microdroplet comprising the probe system was then prepared for use in nozzle group 10 of the apparatus exemplified above. It had a composition corresponding to that derived from the following formulation:

56 uL 5× buffer pH 7.5
28 uL comprising 4 different first oligonucleotides (A, G, C and T selective), 100 nM
28 uL second oligonucleotide, 10 nM
0.4 U Phusion II Hot Start polymerase (exonuclease)
1.6 U Bst Large Fragment polymerase
20 U *E. coli* ligase
Water to 280 uL wherein the 5× buffer comprised the following mixture:

200 uL Trizma hydrochloride, 1M, pH 7.5
13.75 uL aqueous $MgCl_2$, 1M
2.5 uL Dithiothreitol, 1M
50 uL Triton X-100 surfactant (10%)
20 uL Nicotinamide adenine dinucleotide, 100 uM
166.67 uL KCl
Water to 1 mL This droplet was printed into a well on a quartz slide containing an aqueous medium including 2.8 uL of dTTP, 10 nM. Capture of the dTTP and ligation of the second oligonucleotide to the first to form a closed-loop used probe was then carried out in the well by incubating the contents at 37° C. for 50 minutes after which the temperature was increased to 70° C. for a further 50 minutes. Growth in fluorescence of the relevant fluorophore dye was the then observed to occur in the well as the cycle of exonucleolysis and regeneration of the used probe occurred.

The invention claimed is:

1. An apparatus for sequencing a nucleic acid by printing droplets at least some of which contain single nucleotides derived from the nucleic acid characterised by comprising;
   a planar substrate having a face with droplet-receiving locations arranged in at least one track parallel to a first axis defining the substrate;
   a printer head comprising a plurality of droplet-dispensing nozzle groups arranged in line one behind the other and juxtaposed above the droplet-receiving locations so that each nozzle group can in turn dispense a droplet comprised of a different fluid into the droplet-receiving locations;
   a means for stepping the printer head along the first axis relative to the droplet-receiving locations;
   a chamber including a means to receive and hold in place a bead to which the nucleic acid is attached located upstream of the printer head by means of which an ordered stream of single nucleotides is created from the nucleic acid and delivered to a first droplet-dispensing nozzle group;
   at least one source of incident electromagnetic radiation adapted to illuminate the droplet-receiving locations and
   at least one photodetector adapted to detect fluorescence radiation emitted by the single nucleotides present in the droplet-receiving locations after illumination and to generate a data stream characteristic of the single nucleotides and
   a microprocessor for analysing the data stream and generating therefrom the sequence of the nucleic acid.

2. The apparatus of claim 1, wherein the substrate comprises an array of droplet-receiving locations arranged as a plurality of tracks parallel to the first axis.

3. The apparatus of claim 1, the plurality of droplet-dispensing nozzle groups each comprise a plurality of nozzles and wherein the nozzles in a given droplet-dispensing nozzle group are arranged in line along a second axis perpendicular to the first and wherein a distance between each adjacent nozzle in said line is the same or an integral multiple of the distance between adjacent droplet-receiving locations in adjacent tracks.

4. The apparatus of claim 3, further comprising a suction nozzle for removing the droplets and/or the coating from the substrate after the fluorescence radiation has been detected.

5. The apparatus of claim 1, further comprising at least one dispenser for dispensing a droplet-immiscible coating onto the surface of the substrate.

6. The apparatus of claim 1, further comprising at least one second dispenser for dispensing cleaning fluid onto the substrate.

7. The apparatus of claim 1, wherein each droplet-receiving location includes a heater or at least some of the locations share a common heater.

8. The apparatus of claim 1, wherein the substrate and printer head are provided with a wheel or groove and rail arrangement to enable them to prevent lateral movement of one relative to the other.

9. The apparatus of claim 1, wherein the upstream site comprises a chamber provided with a nucleic acid receiving site and an inlet and outlet for receiving an aqueous medium and dispensing it to the printer head.

10. The apparatus of claim 1, wherein the substrate at each droplet-receiving location is optically transparent and that each droplet-receiving location is illuminated by the source of incident radiation on a side of the substrate opposite that which is adjacent to the photodetector.

11. The apparatus of claim 1, wherein the photodetector and source of incident radiation are located on a same side of the substrate.

12. The apparatus of claim 11, further comprising at least one third droplet-dispensing nozzle group.

13. The apparatus of claim 1, wherein the droplet-dispensing nozzle groups are comprised of at least of first and second groups.

* * * * *